United States Patent [19]

Singleton et al.

[11] Patent Number: 4,733,006

[45] Date of Patent: Mar. 22, 1988

[54] CARBONYLATION PROCESS WITH AN ALKALI METAL ACETATE AS CATALYST STABILIZER

[75] Inventors: Thomas C. Singleton, Chesterfield; Frank E. Paulik, Creve Coeur, both of Mo.

[73] Assignee: Monsanto Company, St. Louis, Mo.

[21] Appl. No.: 524,508

[22] Filed: Aug. 18, 1983

Related U.S. Application Data

[63] Continuation-in-part of Ser. No. 221,228, Dec. 29, 1980, abandoned.

[51] Int. Cl.$^4$ .................. C07C 51/10; C07C 51/12; C07C 53/08; C07C 67/36; C07C 67/37

[52] U.S. Cl. .................. 562/519; 260/410.9 R; 260/413; 560/8; 560/97; 560/105; 560/109; 560/114; 560/204; 560/232; 562/406; 562/497; 562/517; 562/520; 562/522

[58] Field of Search .............. 562/519, 517, 520, 406, 562/497; 260/413, 410.9 R; 560/232, 204, 97, 105, 114, 109, 8

[56] References Cited

U.S. PATENT DOCUMENTS

| | | | |
|---|---|---|---|
| 3,579,552 | 5/1971 | Craddock et al. | 260/413 |
| 3,818,060 | 6/1974 | Forster et al. | 260/413 |
| 3,845,121 | 10/1974 | Eubanks et al. | 562/519 |

FOREIGN PATENT DOCUMENTS

| | | | |
|---|---|---|---|
| 1326014 | 8/1973 | United Kingdom | 562/519 |
| 1538782 | 1/1979 | United Kingdom | 560/232 |

*Primary Examiner*—Vivian Garner
*Attorney, Agent, or Firm*—Wendell W. Brooks; Arthur E. Hoffman; Arnold H. Cole

[57] ABSTRACT

The present invention provides for an improved process wherein an olefin, an alcohol, or an ester, halide or ether derivative of said alcohol is reacted with carbon monoxide in a liquid phase in the presence of a catalyst system that contains (a) a rhodium component, and (b) and iodine or bromine component. By passing at least a portion of the liquid reaction mass from the reaction zone to a separation zone of substantially lower CO partial pressure, at least a portion of the carbonylation products, as well as unreacted carbon monoxide, inert gases and unreacted olefin, alcohol or alcohol derivatives are vaporized and can be withdrawn from the separation zone. Precipitation of the rhodium catalyst under carbon monoxide deficient conditions is prevented or retarded by addition to the carbon monoxide deficient zones of the system of a catalyst stabilizer which is a germanium (IV) compound, an alkali metal compound, and mixtures thereof.

5 Claims, No Drawings

CARBONYLATION PROCESS WITH AN ALKALI METAL ACETATE AS CATALYST STABILIZER

CROSS-REFERENCE TO RELATED APPLICATION

This application is a continuation-in-part of our co-pending application Ser. No. 221,228, filed Dec. 29, 1980, now abandoned.

FIELD OF THE INVENTION

The present invention relates to a carbonylation process improvement. More particularly, this invention relates to an improved process scheme wherein at least a portion of the reaction mass from a carbonylation process can be withdrawn from the reactor and separated at a lower pressure from a catalyst-containing stream which is recycled to the reactor. In this processing scheme the catalyst is stabilized in soluble form and any of the catalyst which may have precipitated is reconverted to a soluble form.

DESCRIPTION OF THE PRIOR ART

Recently, processes for producing carboxylic acids and esters by carbonylating olefins, alcohols, esters, halides and ethers in the presence of homogeneous catalyst systems that contain rhodium and halogen components such as iodine components and bromine components have been disclosed and placed into commercial operations. These recently developed processes represent a distinct improvement over the classic carbonylation processes wherein such feed materials have been previously carbonylated in the presence of such catalyst systems as phosphoric acid, phosphates, activated carbon, heavy metal salts and metal carbonyls such as cobalt carbonyl, iron carbonyl and nickel carbonyl. All of these previously known processes require the use of extremely high partial pressures of carbon monoxide. These previously known carbonylation systems also have distinct disadvantages in that they require higher catalyst concentrations, longer reaction times, higher temperatures to obtain substantial reaction and conversion rates that all result in larger and more costly processing equipment and higher manufacturing costs.

The discovery that rhodium and iodine or bromine containing catalyst systems will carbonylate such feed materials as olefins, alcohols and esters, halide or ether derivatives of the alcohols at relatively mild pressure and temperature conditions was a distinct contribution to the carbonylation art. In spite of the vast superiority of these newly developed catalyst systems, it has been found that conventional processing schemes for separation of the carbonylation products from the liquid reaction mass has posted problems of catalyst inactivation and precipitation from carbon monoxide-deficient streams.

It has been disclosed to U.S. Pat. No. 3,845,121 that by withdrawing a portion of the liquid reaction mass from the reactor and passing it to a separation zone of substantially lower pressure, without the addition of heat, at least a portion of the carbonylation products can be vaporized and passed on to purification equipment with much reduced decomposition of the carbonylation catalyst system. According to this scheme, the carbonylation reaction is carried out in the reaction zone at a temperature of from about 50° to about 500° C. and a pressure of from about 345 to about 10340 kPa. By withdrawing a portion of the liquid reaction mass and passing it to a separation zone that is maintained at a pressure that is substantially lower than the pressure in the reactor, at least a portion of the carbonylation products will vaporize with much reduced decomposition of the liquid catalyst system. This vaporization will take place without the addition of heat to the reaction mass. The unvaporized liquid in the separation zone containing the catalyst system can be recycled to the reactor.

Using this processing scheme, it has been found that catalyst precipitation may occur, though to a reduced degree, from liquid streams which are deficient in carbon monoxide. Such streams include the stream of reaction mass withdrawn from the reaction zone, in which CO has been consumed by reaction, and the liquid cycle stream returned from the separation zone to the reaction zone.

From U.S. Pat. No. 3,818,060 it is known that pentavalent nitrogen and phosphorous compounds of the form $XNR_3$ or $XPR_3$ wherein X is oxygen or sulfur may be used as stabilizers for rhodium catalysts in the liquid phase carbonylation of ethylenically unsaturated compounds. Also, from U.S. Pat. No. 3,579,552 it is known that, inter alia, phosphines, amines and trihalostannate compounds form coordination complexes with rhodium and carbon monoxide which remain soluble in the carbonylation of ethylenically unsaturated compounds. Additionally, from British Pat. No. 1,326,014 it is known that stabilizer donor ligands selected from (a) an organic isocyanide, (b) an organic compound (other than an alcohol) containing nitrogen, phosphorus, arsenic, antimony, oxygen, sulfur, or selenium having a lone pair of electrons, or (c) a stannous or germanium (II) halide are useful as stabilizers and activators, for rhodium catalysts in the liquid phase carbonylation of organic alcohols to a carboxylic acid or carboxylic acid ester with carbon monoxide.

Accordingly, it is an object of this invention to prevent precipitation of the soluble catalyst system from CO-deficient streams.

Another object of this invention is to reconvert precipitated components of the catalyst system to soluble form.

Additional objects of this invention will become apparent from the following discussion of the invention.

SUMMARY OF THE INVENTION

The present invention is an improvement in a carbonylation process wherein an olefin, an alcohol, or an ester, halide or ether derivative of said alcohol is reacted with carbon monoxide in a liquid phase in the presence of a catalyst system that contains (a) a rhodium component, and (b) an iodine or bromine component, and in which at least a portion of the carbonylation products are separated from the liquid reaction mass at a reduced CO partial pressure in a separation zone. From this separation zone, an unvaporized liquid stream which is enriched in the catalyst system components is withdrawn and recycled to the reaction zone for reuse in the carbonylation process. A recycle pump is employed to increase the pressure of this liquid stream to enable its transfer back into the higher pressure reaction zone.

Under the conditions of reduced CO partial pressure existing in the separation zone and piping connecting the separation zone to the reaction zone, a small portion of the catalyst system may decompose, forming an insoluble rhodium containing precipitate. According to the present invention, a compound of germanium (IV) or an alkali metal is employed as a catalyst stabilizer for rhodium catalysts in the carbonylation of methanol. Preferably, the stabilizer compound is employed in a molar ratio of at least about 0.5 to the rhodium present.

DESCRIPTION OF THE PREFERRED EMBODIMENT

This invention is directed to the recently developed carbonylation processes wherein olefins, alcohols, and ester, halide and other derivatives of the alcohols are reacted with carbon monoxide in a liquid phase system in the presence of a homogeneous catalyst system that contains (a) a rhodium component, and (b) an iodine or bromine component.

This invention solves the catalyst precipitation problems which may be encountered in the process of separation of the carbonylation products from the liquid mass which involves withdrawing at least a portion of the liquid reaction mass from the reactor and passing it to a separation zone that is maintained at a substantially lower pressure. The lower pressure in the separation zone results in the vaporization of at least a portion of the carbonylation products which are then withdrawn from the separation zone in the vapor form. The unvaporized liquid in the separation zone containing the stable catalyst system can then be recycled to the reactor for reuse in the carbonylation process. According to this invention, the rhodium carbonyl halide catalyst complex is stabilized by addition of a germanium (IV) compound, an alkali metal compound, and mixtures thereof. The stabilizer compound is employed in a molar ratio of at least 0.5 to the rhodium present.

When reference is made to the "catalyst system" throughout this disclosure of this invention, it means a catalyst system that forms on combining two distinct components in the presence of carbon monoxide. The two essential catalyst precursor materials are (a) a rhodium component, and (b) an iodine or bromine component while CO is a third component.

Rhodium components suitable for use as constitutents in the catalyst are described and set out in U.S. Pat. No. 3,845,121, the disclosure of which is incorporated herein by reference.

The iodine or bromine precursor component of the catalyst system used herein may be in combined form with the rhodium as, for instance, one or more liquids in a coordination compound of the rhodium. However, it is generally preferred to have an excess of the iodine or bromine present in the reaction system over the iodine or bromine that exists as ligands of the rhodium compounds. The bromine or iodine precursor can be in the form of elemental bromine or iodine as well as combinations of bromine or iodine such as hydrogen iodide, hydrogen bromide, alkyl iodide, alkyl bromide, aryl iodide, aryl bromide, iodide salts, bromide salts and the like. Suitable non-limiting examples of such compounds of bromine and iodine include methyl iodide, methyl bromide, ethyl iodide, ethyl bromide, sodium iodide, potassium iodide, sodium bromide, potassium bromide, ammonium iodide, ammonium bromide and the like.

Generally, it is preferred that the amount of iodine precursor material added to the reaction system will be in an amount such that the atomic ratio of the iodine or bromine to the rhodium is above 2:1. Preferably, the atomic ratio of the iodine or bromine to the rhodium will be in a range of 5:1 to 5000:1. A more preferred atomic ratio of the iodine or bromine to the rhodium is 10:1 to 2500:1.

Suitable non-limiting stabilizer compounds, according to this invention, are the halides, acetates, oxides, salts and the like of germanium (IV) and alkali metals.

The catalyst system forms by combining the foregoing rhodium and halogen in the presence of carbon monoxide in a liquid reaction medium. The liquid reaction medium employed may include any solvent compatible with the catalyst system and may include pure alcohols or mixtures of the alcohol feedstock and/or the desired carboxylic acid and/or esters of these two compounds. However, the preferred solvent or liquid reaction medium for the process of this invention is the desired carbonylation products such as the carboxylic acid and/or ester of the acid and an alcohol. Water is also often in the reaction mixture to exert a beneficial effect upon the reaction rate.

Suitable feedstock materials for the process are set out in U.S. Pat. No. 3,845,121 previously incorporated by reference.

Methanol and ethylene are two of the most preferred feedstocks that are utilized in the practice of our invention.

In carrying out the carbonylation reaction, the above-mentioned feedstocks are intimately contacted with carbon monoxide in a liquid reaction medium that contains the above-mentioned catalyst system. The catalyst system can be preformed outside of the reactor by combining the necessary catalyst precursors or it can be formed in situ. Generally, the catalyst will be employed in such amounts as to provide a concentration of soluble rhodium in the reaction medium of from about 10 ppm to about 3000 ppm depending upon the equipment size, desired reaction time and other factors. The carbon monoxide reactant can be sparged into the reactor in such a manner as to intimately contact the carbon monoxide with the reactants in the reaction mass. The pressure in the reactor will generally be maintained in the range of from 345 to about 10340 kPa. As disclosed in the prior art, the foregoing known carbonylation process is carried out at a temperature range of from about 50° C. to about 500° C. with a preferred temperature range of from about 100° C. to about 250° C. The optimum temperature and pressure maintained in the reactor will vary depending upon the reactants and the particular catalyst system utilized. The catalyst, feedstock materials and general reaction parameters set out in the foregoing discussion are known in the art.

A portion of the liquid phase reaction mass is withdrawn from the reactor and passed to a separation zone that is maintained at a pressure that is lower than the reactor pressure. This pressure reduction will cause at least a portion of the carbonylation products to vaporize and separate from the unvaporized residue of the liquid reaction mass. The aforementioned catalyst system will remain in this residue of unvaporized liquid reaction mass and can be recycled to the reactor.

Generally, it is preferred that the separation zone be maintained at a pressure of at least 138 kPa lower than the pressure in the reactor. The pressure in the reaction is usually in the range of about 345 to 10340 kPa. Thus, the separation zone is maintained at a pressure less than 10200 kPa. It has been found that the separation zone can be maintained at very low pressure, even approaching a complete vacuum; however, it is usually desirable that the separation zone be maintained at a positive pressure to eliminate vapor compression equipment and the like in handling the vaporized carbonylation products that are withdrawn from the separation zone. By maintaining pressure differential of at least 138 kPa between the reactor and the separation zone, a substantial amount of the carbonylation products can be vaporized from the liquid reaction mass.

The exact pressure of the separation zone will vary, depending on the temperature and pressure maintained in the reactor. It is important that the pressure differential between the separation zone and the reactor be at least 138 kPa to insure vaporization of a substantial portion of the carbonylation products in the separation zone. It is also important that the total pressure in the separation zone be less than the vapor pressure of the carbonylation products in the liquid reaction mass withdrawn from the reactor at the temperature of the liquid reaction mass. For example, if at the temperature and pressure of the reactor the carbonylation products to be vaporized have a vapor pressure of 1380 kPa, the separation zone should be operated at a pressure of less than 1240 kPa. Preferably, the separation zone of this invention will be operated at a pressure of from about 69 to 1380 kPa. Most preferably, the separation zone will be operated at a pressure of about 100 to 690 kPa.

The separation zone should be large enough to allow the liquid reaction mass that is passed to it from the reactor to be maintained in said separation zone for a sufficient period of time to vaporize the desired carbonylation products, prior to recycling the unvaporized liquid containing the homogeneous catalyst system back to the reactor. Usually, a residence time of at least one minute in the separation zone is sufficient.

Following separation of the desired carbonylation products, the unvaporized liquid portion of the reaction mass containing any precipitated catalyst decomposition products leaves the separation zone and is introduced into the suction of a recycle pump which increases the pressure of this stream sufficiently to permit its injection back into the reaction zone.

The piping through which a portion of the reaction mass is withdrawn from the reaction zone, as well as the piping through which the liquid recycle stream is transferred back to the reaction zone by the recycle pump, will be at substantially the pressure of the reaction zone. As used herein, "substantially the pressure of the reaction zone" means the reaction zone pressure plus or minus pressure changes caused by fluid flow through the respective lines.

Depending upon the temperature and pressure of the transfer piping, a minor amount of the carbonylation catalyst system according to the prior art (i.e., not including the stabilizer component of the present invention) may decompose and precipitate from the liquid in the piping. The catalyst system is believed to comprise a carbonyl complex of the rhodium component and the halide component and it is further believed that carbon monoxide may be abstracted from a portion of the carbonyl complex form of the catalyst system converting some of the catalyst to an insoluble form which may comprise a rhodium halide. Because the rhodium component of the catalyst system is quite expensive, it is desirable to recover any traces of precipitated catalyst for return to the reaction zone and reuse.

According to the present invention, the rhodium catalyst is maintained in soluble form in these carbon monoxide deficient portions of the process by addition to the system of a germanium (IV) compound, an alkali metal compound, and mixtures thereof.

The stabilizer compound is employed in a molar ratio of at least about 0.5 to the rhodium present in the catalyst system. The stabilizer compound may be injected into the carbonylation reaction system at any convenient point, but is preferably injected into the transfer piping leading from the carbonylation reactor to the separation zone, or into the piping which conducts the catalyst-containing recycle stream from the separation zone back to the reactor, in order to insure complete mixing of the stabilizer with the catalyst-containing liquid system. That is, the stabilizer compound may be conveniently injected into or added to the carbon monoxide deficient zones of the carbonylation system.

The practice of this invention is illustrated by the following examples which should not be construed as limiting the invention in any way.

In the following examples a stock solution was prepared which simulates the liquid recycle stream which is returned from the separation zone to the carbonylation reactor in a typical acetic acid plant. Included in this solution were traces of iron, nickel, chromium and molybdenum which are normally found in acetic acid plants as corrosion products. The stock solution employed acetic acid as the solvent and contained the following:

| | |
|---|---|
| Iron | 0.025 moles/liter |
| Nickel | 0.02 moles/liter |
| Chromium | 0.016 moles/liter |
| Water | 9.5 moles/liter |
| Total iodide | 0.5 moles/liter |
| Labile methyl groups (methanol + methyl iodide + methyl acetate) | 0.35 moles/liter |

EXAMPLE 1

To establish a base run in which no stabilizer was present, the following experiment was performed. About 650 milliliters of the stock solution described above plus a rhodium solution and hydrogen iodide was charged into a 1500 milliliter stirred autoclave and pressured with carbon monoxide to a pressure of 791 kPa. The contents were heated with stirring and when a temperature of 150°–155° C. was reached, methanol and methyl iodide were added. The autoclave contents were then immediately cooled to about 125°–128° C. under a pressure of 205 kPa and maintained in a refluxing condition. The initial dissolved rhodium content, was 444 ppm.

The autoclave contents were sampled periodically and analyzed for dissolved rhodium. The results of these analyses were as follows:

| Time After Methanol Addition (minutes) | ppm Dissolved Rhodium | % of Original Dissolved Rhodium |
|---|---|---|
| 63 | 249 | 56 |
| 93 | 166 | 37 |

This experiment clearly demonstrates that in the absence of a catalyst stabilizer the rhodium rapidly precipitates from the solution in the autoclave.

EXAMPLE 2

Using the equipment and procedure of Example 1, the base case run was repeated except that the autoclave solution contained 0.0045 moles/liter of $GeI_4$. Total iodine and total labile methyl groups were as in Example I initially. After 85 minutes at a temperature of 128°–129° C., the solution was analyzed and found to contain 379 ppm dissolved rhodium or 85% of the original dissolved rhodium.

These results clearly indicate that the stabilizer greatly retarded the rate of rhodium precipitation from the autoclave solution.

EXAMPLE 3

The experiment of Example 2 was repeated except that the autoclave solution contained 0.2 moles/liter of lithium acetate and 0.7 moles/liter total iodide. Autoclave temperature was 126°–128° C. Periodic sampling for dissolved rhodium gave the following results:

| Time After Methanol Addition (minutes) | ppm Dissolved Rhodium | % of Original Dissolved Rhodium |
| --- | --- | --- |
| 61 | 318 | 72 |
| 91 | 249 | 56 |

EXAMPLE 4

The experiment of Example 1 was repeated using as a stabilizer 0.2 mole/liter of potassium iodide. After 124 minutes of refluxing at 128°–129° C., the solution was analyzed and found to contain 228 ppm or 51% of the original dissolved rhodium.

EXAMPLE 5

To establish another base run under different conditions in which no stabilizer was present, the following experiment was performed. About 650 milliliters of a stock solution containing 0.027 moles/liter iron, 0.019 moles/liter nickel, 0.014 moles/liter chromium, 0.007 moles/liter molybdenum, 1.40 moles/liter total iodide, 8.9 moles/liter water and 1.44 moles/liter labile methyl groups using acetic acid as the solvent plus a rhodium solution and hydrogen iodide was charged into a 1500 milliliter stirred autoclave and pressured with carbon monoxide to a pressure of 791 kPa. The contents were heated with stirring and when a temperature of 185° C. was reached methanol and methyl iodide were added. Temperature was maintained at 185° C.

The autoclave contents, which initially contained 416 ppm dissolved rhodium, were sampled and analyzed for dissolved rhodium after 61 minutes. Dissolved rhodium ran 168 ppm or 40% of the original.

Again, this experiment clearly demonstrates that in the absence of a catalyst stabilizer the rhodium rapidly precipitates from the solution in the autoclave.

EXAMPLE 6

The procedure of Example 5 was repeated using the stock solution of that Example and using $GeI_4$ as the stabilizer compound. The results were as shown below:

| Example | Catalyst Stabilizer | Time (minutes) | ppm Dissolved Rhodium | % Of Original Dissolved Rhodium |
| --- | --- | --- | --- | --- |
| 6 | 0.018 moles/ liter $GeI_4$ | Initial 61 | 392 286 | 73 |

What is claimed is:

1. In a carbonylation process wherein at least one reactant selected from the group consisting of an alcohol, an ester derivative of said alcohol, a halide derivative of said alcohol and an ether derivative of said alcohol is (1) reacted with carbon monoxide in a liquid phase in a reaction zone and in the presence of a catalyst system that contains (a) rhodium component, and (b) an iodine or bromine component, (2) passing at least a portion of the liquid reaction mass in which the carbon monoxide has been depleted from the reaction zone to a separation zone, and (3) recycling the remaining liquid reaction mass from the separation zone to said reaction zone, the improvement which comprises supplying to the carbon monoxide deficient zones of the process a separately added catalyst stabilizer soluble in said reaction mass in an amount sufficient to maintain the rhodium component in soluble form, said catalyst stabilizer being an alkali metal acetate.

2. The process of claim 1 wherein the catalyst system contains a rhodium component and an iodine component.

3. The process of claim 1 wherein methanol is carbonylated to acetic acid.

4. The process of claim 1 wherein the catalyst stabilizer is present in a molar ratio of at least 0.5 to the rhodium component.

5. The process of claim 1 wherein the alkali metal acetate is lithium acetate.

* * * * *